United States Patent [19]

Pinkowski

[11] Patent Number: 5,736,029
[45] Date of Patent: Apr. 7, 1998

[54] AMPEROMETRIC DUAL-ELECTRODE SENSORS

[75] Inventor: Alexander Pinkowski, Schönbrunn-Haag, Germany

[73] Assignee: Prominent Dosiertechnik GmbH, Heidelberg, Germany

[21] Appl. No.: 762,338

[22] Filed: Dec. 9, 1996

[30] Foreign Application Priority Data

Dec. 20, 1995 [DE] Germany .................. 195 47 670.0

[51] Int. Cl.$^6$ ...................................................... G01N 27/26
[52] U.S. Cl. ............ 205/789; 205/789.5; 205/777.5; 204/400; 204/403; 204/416; 204/435; 204/293; 422/82.03
[58] Field of Search ................................ 204/293, 435, 204/400, 403, 416; 205/789, 789.5, 777.5; 422/82.03

[56] References Cited

U.S. PATENT DOCUMENTS

| | | |
|---|---|---|
| 3,000,805 | 8/1961 | Carritt et al. ........................ 204/415 |
| 3,141,835 | 7/1964 | Rolin et al. .......................... 204/400 |
| 3,291,705 | 12/1966 | Hersch ................................. 204/431 |
| 4,187,162 | 2/1980 | Dageforde ........................... 204/195 |
| 4,605,900 | 8/1986 | Moilanen et al. .................... 324/439 |

FOREIGN PATENT DOCUMENTS

| | | |
|---|---|---|
| 2 692 675 | 12/1993 | France . |
| 2 327 825 | 12/1974 | Germany . |
| 3316670 A1 | 11/1983 | Germany . |
| 686980 XP | 12/1993 | Liechtenstein . |
| 000646194 XP | 5/1982 | Netherlands . |
| 000647166 | 5/1982 | Netherlands . |

*Primary Examiner*—Bruce F. Bell
*Attorney, Agent, or Firm*—Darby & Darby

[57] ABSTRACT

An amperometric dual-electrode sensor having an operating electrode inside a passivable metal electrode used as the counter electrode is provided by the invention. A method for measuring the concentration of a compound or ions in a sample is also provided by this invention. In particular, a method of measuring hydrogen peroxide in a sample is described.

17 Claims, 1 Drawing Sheet

AMPEROMETRIC DUAL-ELECTRODE SENSORS

FIELD OF THE INVENTION

This invention relates generally to amperometric dual-electrode sensors. More specifically, this invention relates to sensors having an operating electrode and a passivable metal used as the counter electrode, which are capable of measuring compounds such as hydrogen peroxide.

BACKGROUND OF THE INVENTION

Amperometric sensors have been on the market in both three-electrode configurations and two-electrode configurations. Three-electrode sensor designs generally consist of an operating electrode, a reference electrode and a counter electrode. A two-electrode (or dual-electrode) design consists of an electrode which performs the functions of both the reference and counter electrode, and a second operating electrode.

In the three-electrode configuration, the concentration of a compound or ions in a sample is generally measured by applying an operating potential between the operating electrode and the reference electrode using potentiostatic circuitry and measuring the amperometric current generated between the operating electrode and the counter electrode. The current generated is proportional to the concentration of the compound or ions in the sample. This current does not flow through the reference electrode and therefore, does not affect the potential of the reference electrode.

The operating electrode for a dual-electrode sensor usually comprises a precious-metal, such as gold or platinum. The other electrode, which serves as both the counter electrode and the reference electrode, is often made of silver/silver chloride. In the two-electrode configuration, an operating potential is run using potentiostatic circuitry between the operating electrode and the electrode which functions as both the reference electrode and counter electrode. The amperometric current generated between the operating electrode and the counter electrode is measured. Thus, in contrast to the three-electrode configuration, current flows through the counter electrode. To accurately assay the sample, in addition to the amperometric current generated, a constant potential must be maintained between the operating electrode and reference electrode to provide a reference value for the operating electrode. This may be accomplished in two ways, for example, in a two electrode sensor using silver chloride. First, the amount of silver chloride on the silver electrode is sufficient to cover the silver electrode at all times with silver chloride, even in the current-conducting state. Second, the silver/silver-chloride electrode is in contact with an internal electrolyte which displays a constant level of chloride-ion activity. This may be accomplished using a KCl solution as the internal electrolyte. The internal electrolyte space is shielded from the measuring medium using, for example, a diaphragm permeable to the substance under analysis. These electrodes are referred to as secondary-type electrodes.

Three-electrode sensors used to detect hydrogen peroxide have been described. A commonly used sensor consists of an operating electrode of a precious metal, a reference electrode using a silver/silver-chloride system, and a counter electrode made from a precious-metal or a high-grade alloy steel. When steel is used, an internal electrolyte is not necessary. If sufficiently conductive, the measuring medium itself can serve as the ion-conducting connection between the operating electrode and the counter electrode. The operation of such a system does not require a diaphragm.

In theory, two-electrode sensors to detect hydrogen peroxide could also be configured having a secondary-type electrode, made for instance, with silver/silver-chloride and KCl as the counter electrode and reference electrode. This configuration requires an enclosed reference electrolyte space to prevent mixing the internal electrolyte with the measuring medium. A suitable membrane or diaphragm may be used.

Both electrode configurations have drawbacks. The three-electrode sensors are intrinsically corrosion-prone at the three electrical contacts by virtue of their exposure to the measuring medium or the ambient atmosphere. All three electrodes are possible points of failure in this sensor.

A dual-electrode system has fewer electrodes and thus fewer contacts; however, this configuration requires an internal electrolyte and a diaphragm, which are sources of possible failure. For example, the secondary electrode may fail due to electrolyte leakage or gas-bubble accumulations between the diaphragm and the operating electrode, which leads to a reduction of the effective operating electrode surface and requires recalibration or the replacement of the diaphragm and the internal electrolyte.

It is an object of this invention to provide a two-electrode sensor which does not require an internal electrolyte or the traditional secondary-type electrode.

It is a further object of the invention that the amperometric dual-electrode sensor has a counter electrode designed as a passivable metal electrode.

It is a further object of the invention that the sensor be designed to operate with or without a diaphragm.

It is a further object of the invention that the counter electrode has an active surface that is substantially larger than the operating electrode.

It is a further object of the invention that the counter electrode is designed in tubular form with an operating electrode inside the counter electrode.

It is a further object of this invention to provide a method for measuring the concentration of a compound or ions in a sample, and in particular, hydrogen peroxide.

SUMMARY OF THE INVENTION

In accordance with the objects of the invention, an amperometric dual-electrode sensor is provided having an operating electrode and a passivable metal electrode used as the counter electrode. The counter electrode is designed in tubular form and performs the function of the reference electrode.

A method for measuring the concentration of a compound or ions in a sample is also provided by this invention. In particular, a method of measuring hydrogen peroxide in a sample is described.

The foregoing and other objects and advantages of this invention will become apparent to those skilled in the art upon reading the detailed description of the preferred embodiments in conjunction with a review of the appended drawings.

DETAILED DESCRIPTION OF THE PREFERRED EMBODIMENTS

Figure 1:
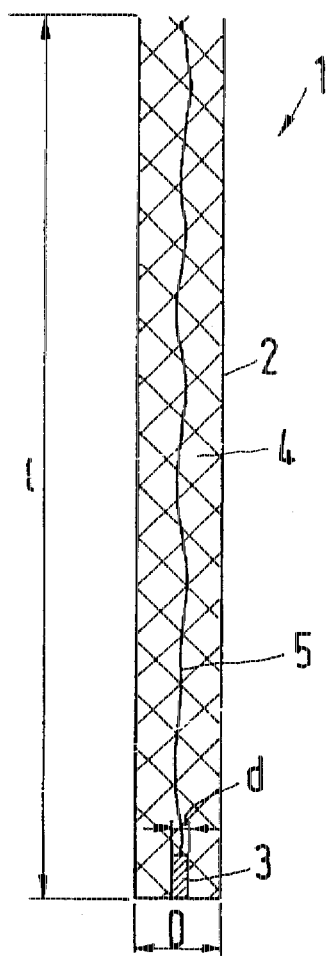
FIG. 1 is a schematic cross section through a dual-electrode sensor according to the present invention.
Figure 2:
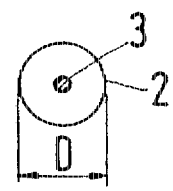
FIG. 2 is a top view of the end of the sensor according to the present invention.

The dual-electrode sensor of this invention can be operated with or without a diaphragm. The diaphragm merely serves to protect the operating electrode from the sample, impeding diffusion of the sample into the pores of the diaphragm, keeping the amperometric signal flow independent. By virtue of the passivation of the counter electrode, the counter electrode obtains a metallic surface that is characterized by substantially reduced reactivity to a given medium.

Without being bound to one theory, it is believed that when a passivated metal electrode is used as the counter electrode in a sensor, without an internal electrolyte or a secondary-type electrode, the passivated counter electrode possesses a potential so stable that it can serve as a constant reference electrode potential in spite of the weak current flow. Specifically, despite the flow of the measuring current, the counter electrode is not significantly polarized, if at all. It is believed that the potential which builds up at the phase boundary between the passivated counter electrode and the sample displays characteristic properties similar to those of the potential of a secondary-type electrode, i.e. the properties typical of a standard reference electrode. A current-conducting counter electrode consisting of a passivated metal is, de facto, suitable for use as a reference electrode similar to conventional secondary-type electrodes even without having its own internal reference electrolyte.

In a preferred embodiment, the counter electrode consists of a high-grade alloy steel such as, for example, steel type 1.4571. Alloy steel has several advantages over the precious metals traditionally used. For example, alloy steel is inexpensive and is relatively easy to passivate, making it possible to produce a low-cost amperometric dual-electrode sensor.

The counter electrode is preferably oxidized. Moreover, it is preferred that the counter electrode have an active surface that is substantially larger than that of the operating electrode. For example, the active surface of the counter electrode may be ten times larger than that of the operating electrode. One skilled in the art is capable of easily estimating the surface size ratio based on the fact that, if current density is held low, it will not cause a polarization of the counter electrode to the point where it would interfere with the results. Typical surface size ratios lie in the range from approximately several hundred to more than several thousand to one.

The design of the counter electrode is preferably tubular, with the operating electrode positioned inside the counter electrode, and the operating electrode covered along its length with an insulating layer, separating it from the counter electrode. The sensor design of this invention offers several advantages over conventional dual-electrode sensor designs. For example, it permits establishing the desired size ratio between the counter electrode and the operating electrode. Moreover, the operating electrode is covered in the longitudinal direction with an insulating layer, which prevents it from coming in contact with the sample. Additionally, the insulating layer provides electrical insulation between the operating electrode and the counter electrode. The tube, which constitutes the counter electrode, can be entirely immersed in the sample, allowing a very large surface exposure which keeps the current density down.

It is preferred that the insulating layer fill at least most of the space between the operating electrode and the counter electrode. The insulating layer thus also acts as a mechanical support for the operating electrode inside the counter electrode.

The present invention further relates to a method for measuring the concentration of a compound or ions in a sample using the dual-electrode sensor described in accordance with the present invention. In the method of this invention, the sensor is immersed in the sample and an operating potential is applied between the operating electrode and the counter electrode and a test current is subsequently measured. The counter electrode is a passivated metal electrode that permits direct immersion of the sensor in the sample.

The method of this invention only requires two electrodes, the operating electrode and the counter electrode. The counter electrode performs the function of a reference electrode without the need for an internal electrolyte in the counter electrode or a secondary-type electrode used in conventional dual-electrode sensors. This makes the measuring process quite simple. The concentration of the substance under analysis in the sample can be determined based on the magnitude of the test current. While the analysis is generally performed as traditionally run, the method of this invention is quick, simple, accurate, and involves considerably less hardware.

In a preferred embodiment, the counter electrode is passivated as it is immersed in the measuring solution. At the outset, the counter electrode consists of a passivable metal. Once the counter electrode is immersed in the sample, the sample reacts with the metal, thereby producing the desired passivating layer.

In an alternative embodiment, the passivation can be obtained by oxidation in air, by chemical oxidation in aqueous liquids or by electrochemical anodic oxidation. These are all relatively simple processes which practically require nothing that would add to the complexity of the system and are understood by the skilled artisan.

Prior to assaying the sample, the physical-chemical surface condition which catalyzes the desired reaction is determined to provide a standard condition before every measurement, thus making these measurements highly reproducible. The surface condition may be determined by potential-jump activation, also referred to as pulse amperometric detection (PAD activation). In this method, anodic and cathodic potentials, which produce the desired defined physical-chemical surface condition on the surface of the operating electrode, are applied prior to applying the actual operating potential. The PAD technique has generally been employed solely for activating the operating electrode. In the method of this invention, the PAD techniques also provide anodic repassivation of the counter electrode during the activation of the operating electrode. It thus serves to create the desired starting condition for both electrodes.

Referring now to the drawings, FIG. 1 shows a sensor 1 having a tube 2 of high-grade alloy steel (Steel type 1.4571) with a length 1 of about 120 mm and an outer diameter D of about 12 mm. The tube 2 doubles as the counter electrode and the reference electrode.

In the center of the tube is a platinum wire 3 having a diameter d of approximately 1 to 2 mm. The length of the platinum wire 3 is of no particular importance. The tube 2 is filled with a compound 4 which serves as an isolating and insulating layer between the platinum wire 3 and the tube 2, thereby providing electrical insulation between these two elements while at the same time mechanically holding the platinum wire 3 in place inside the tube 2. The compound may be any conventional compound capable of isolating and insulating the platinum wire from the tube. The platinum wire 3 only need be long enough to be securely held in place by the compound 4.

The end of the platinum wire 3 is not covered by the compound 4. One approach to assure that the end of the platinum wire 3 is exposed is to grind the end of the sensor 1 either in planar, spherical or conical fashion, in a way that the compound 4, the platinum wire 3 and the tube 2 terminate at the same point.

The platinum wire 3 is connected to an evaluation system 5 using an electrical conductor 5, not shown in detail. The tube 2 is also electrically connected to an evaluation system.

In the sensor of the present invention, the platinum wire 3 serves as the operating electrode and the tube 2 serves as both the counter electrode and the reference electrode.

The tube 2 of the electrode of this invention has a passivable surface, which is passivated prior to the actual measuring process. Passivation can be achieved, for example, by oxidation in air, by chemical oxidation in aqueous liquids, or by electrochemical anodic oxidation.

Hydrogen peroxide in water may be detected using the sensor of this invention having a high-grade alloy steel counter electrode. The oxidative passivating layer is chemically formed on the surface by virtue of the oxidizing effect of the hydrogen peroxide contained in the measuring liquid. The passivation takes place when the sensor comes into contact with water. The passivation of the counter electrode thus takes place in situ as the sensor is immersed in the water containing hydrogen peroxide.

A low current is generated between the operating electrode and the counter electrode when a sample is tested. There is little to no polarization of the counter electrode during the passivation process. Therefore, the reference potential remains largely unchanged. Specifically, it has been discovered in accordance with this invention that when the diameter of the operating electrode is approximately 2 mm, the surface ratio between the counter electrode and the operating electrode is about 360:1. When the diameter is approximately 1 mm, the ratio is about 1,440:1. One skilled in the art would appreciate that the typical sensitivity levels of amperometric sensors (i.e. the so-called slope of the sensor) having an operating electrode with a diameter of 1 mm is on the order of nA/ppm. Therefore, when a sample analysis has a low concentration in the neighborhood of 1 ppm, the current density (meaning the current intensity per surface unit) on the operating electrode is generally less than 10 $nA/cm^2$. Thus, a one thousand times larger counter electrode would have a current density less than 10 $pA/cm^2$. When the current density level on the counter electrode is less than 10 $pA/cm^2$, the amperometric current flow will not polarize the counter electrode.

In a preferred embodiment, the sensor is designated to measure hydrogen peroxide in a sample. The sensor consists of a platinum operating electrode and an alloy-steel counter electrode. The activating potentials typically involve a cathodic reductive cleaning phase of the operating electrode at about 0±50 mV, followed by an anodic oxidative coating of the operating electrode surface at about −1100±100 mV. The potentials indicated refer to the potential of the operating electrode in relation to the counter electrode. Since the amperometric conversion of hydrogen peroxide tends to take place primarily on the oxide-coated operating electrode, the sequence of the activation potentials must be selected as stated above (i.e. reductive cleaning first, followed by oxidative coating, then the measuring process). The preferred time ratios for the two activation steps (i.e. between reduction and oxidation) are approximately 2:1 to 10:1.

While the embodiments of the invention shown and described are fully capable of achieving the results desired, it is to be understood that these embodiments have been shown and described for purposes of illustration only and not for purposes of limitation.

What is claimed is:

1. An amperometric two-electrode sensor, comprising an operating electrode and a combination reference and counter electrode, wherein the counter electrode is a passivable metal electrode and the sensor is devoid of an internal electrolyte and secondary electrode.

2. The sensor of claim 1, wherein the counter electrode comprises a high-grade alloy steel.

3. The sensor of claim 1, wherein the counter electrode is oxidized.

4. The sensor of claim 1, wherein the counter electrode has an active surface substantially larger than the operating electrode.

5. The sensor of claim 1, wherein the counter electrode has a tubular body containing the operating electrode.

6. The sensor of claim 5, wherein the operating electrode is covered in the longitudinal direction with an insulating layer which separates the operating electrode from the counter electrode.

7. The sensor of claim 6, wherein the insulating layer fills the space between the operating electrode and the counter electrode.

8. A method for measuring the concentration of a compound or ions in a sample comprising immersing the sensor of claim 1 into a sample, applying an operating potential between the operating electrode and the counter electrode and measuring the test current generated, wherein the counter electrode is passivated as it is immersed in the sample.

9. The method of claim 8, wherein the physical-chemical surface condition is determined prior to measuring the sample.

10. The method of claim 9, wherein the physical-chemical surface condition is determined using potential-jump activation.

11. The method of claim 8, wherein the counter electrode comprises a high-grade alloy steel.

12. The method of claim 8, wherein the counter electrode is oxidized.

13. The method of claim 8, wherein the counter electrode has an active surface substantially larger than the operating electrode.

14. The method of claim 8, wherein the counter electrode has a tubular body containing the operating electrode.

15. The method of claim 14, wherein the operating electrode is covered in the longitudinal direction with an insulating layer which separates the operating electrode from the counter electrode.

16. The method of claim 8, wherein the compound is hydrogen peroxide.

17. A method for measuring the concentration of a compound or ions in a sample comprising immersing the sensor of claim 1 into a sample, applying an operating potential between the operating electrode and the counter electrode and measuring the test current generated, wherein the counter electrode is passivated prior to being immersed in the sample by the air, by chemical oxidation or by electrochemical anodic oxidation.

* * * * *